United States Patent
Kraft et al.

(10) Patent No.: US 11,845,849 B2
(45) Date of Patent: Dec. 19, 2023

(54) PROCESS FOR PREPARING DIALKYL 1,4-CYCLOHEXANEDICARBOXYLATES

(71) Applicant: Evonik Operations GmbH, Essen (DE)

(72) Inventors: Johannes Kraft, Niederkassel (DE); Lena Altmann, Dorsten (DE); Johan Anton, Dorsten (DE); Michael Grass, Haltern am See (DE); Thomas Schneider, Schermbeck (DE)

(73) Assignee: Evonik Operations GmbH, Essen (DE)

( * ) Notice: Subject to any disclaimer, the term of this patent is extended or adjusted under 35 U.S.C. 154(b) by 192 days.

(21) Appl. No.: 17/385,323

(22) Filed: Jul. 26, 2021

(65) Prior Publication Data

US 2022/0033618 A1 Feb. 3, 2022

(30) Foreign Application Priority Data

Jul. 28, 2020 (EP) .................................. 20188048

(51) Int. Cl.
| | |
|---|---|
| *C08K 5/12* | (2006.01) |
| *C09D 7/63* | (2018.01) |
| *B01J 21/06* | (2006.01) |
| *B01J 23/46* | (2006.01) |
| *C07C 51/36* | (2006.01) |
| *C09J 11/06* | (2006.01) |

(52) U.S. Cl.
CPC .............. *C08K 5/12* (2013.01); *B01J 21/063* (2013.01); *B01J 23/462* (2013.01); *C07C 51/36* (2013.01); *C09D 7/63* (2018.01); *C09J 11/06* (2013.01)

(58) Field of Classification Search
CPC ....... B01J 21/063; B01J 23/462; C07C 51/36; C07C 67/303; C07C 69/75; C08K 5/12; C09D 7/63; C09J 11/06; G09G 2300/0426; G09G 2300/0819; G09G 2300/0842; G09G 2310/08; G09G 2320/0257; G09G 2330/02; G09G 2330/021; G09G 2330/025; G09G 2330/12; G09G 3/32; G09G 3/3208; G09G 3/3225; G09G 3/3233; Y02P 20/582

See application file for complete search history.

(56) References Cited

U.S. PATENT DOCUMENTS

| | | | |
|---|---|---|---|
| 2006/0167151 A1* | 7/2006 | Grass | .................... C07C 67/303 524/285 |
| 2017/0015810 A1* | 1/2017 | Miyazaki | .................. C08J 5/18 |

FOREIGN PATENT DOCUMENTS

| | | | |
|---|---|---|---|
| CN | 105037161 | * | 11/2015 |
| EP | 1676828 | | 7/2006 |
| EP | 3085686 | | 10/2016 |
| WO | 2015/093849 | | 6/2015 |

OTHER PUBLICATIONS

CN105037161 translated (Year: 2015).*
Schwidder et al. (published 1987, 3 pages) (Year: 1987).*
European Search Report dated Jan. 14, 2021 in Application No. 20188048.1, 5 pages.

* cited by examiner

*Primary Examiner* — Yevgeny Valenrod
*Assistant Examiner* — Blaine G Doletski
(74) *Attorney, Agent, or Firm* — Grüneberg and Myers PLLC

(57) ABSTRACT

A process prepares dialkyl 1,4-cyclohexanedicarboxylates by ring hydrogenation of the corresponding dialkyl terephthalate having a CO value of less than 0.3 mg KOH/g. The dialkyl 1,4-cyclohexanedicarboxylates thus produced can be used as plasticizers or as a component of a plasticizer composition for plastics, in particular PVC.

19 Claims, No Drawings

PROCESS FOR PREPARING DIALKYL 1,4-CYCLOHEXANEDICARBOXYLATES

CROSS-REFERENCE TO RELATED APPLICATIONS

This application claims priority to European Patent Application No. 20188048.1, filed Jul. 28, 2020: the content of which is hereby incorporated by reference in its entirety.

BACKGROUND OF THE INVENTION

Field of the Invention

The present invention relates to a process for preparing dialkyl 1,4-cyclohexanedicarboxylates by ring hydrogenation of the corresponding dialkyl terephthalate having a CO value of less than 0.3 mg KOH/g. The invention also provides for the use of the dialkyl 1,4-cyclohexanedicarboxylates thus produced as plasticizers or as a component of a plasticizer composition for plastics, in particular PVC.

Description of Related Art

Plasticizers are used in many industrial fields in order to make plastics such as polyvinyl chloride (PVC) softer and more flexible. Phthalates, that is to say the diesters of (ortho-)phthalic acid, have for many years been the dominant plasticizer class. However, in recent years there has also been an increase in the significance of the alkyl esters of cyclohexanedicarboxylic acids, not least on account of the debate around possible health concerns of phthalate-based plasticizers. The primary role is here played by dialkyl 1,2-cyclohexanedicarboxylates, and more recently by dialkyl 1,4-cyclohexanedicarboxylates too.

Dialkyl 1,2-, 1,3- and 1,4-cyclohexanedicarboxylates can be prepared by hydrogenation of the aromatic ring of the corresponding phthalates, isophthalates or terephthalates (hereinafter ring hydrogenation). Ring hydrogenations of this kind are in some cases already being carried out on an industrial scale, for example for the production of DINCH, the diisononyl ester of 1,2-cyclohexanedicarboxylic acid.

The rate of reaction of the ring hydrogenation is a key factor in the profitability of the process, since investment costs and operating costs are both influenced by this.

SUMMARY OF THE INVENTION

The object of the present invention was therefore to provide a process for preparing dialkyl 1,4-cyclohexanedicarboxylates with which the rate of hydrogenation can be kept at a high level and the productivity of the hydrogenation process accordingly increased.

It has now surprisingly been found that dialkyl terephthalates in which the alkyl groups both have at least 2 carbon atoms, preferably at least 4 carbon atoms, can be readily and swiftly hydrogenated when the carbonyl value thereof (CO value) does not exceed a defined value. The use of appropriate dialkyl terephthalates in the ring hydrogenation accordingly increases productivity and thus profitability of the process too.

The process of the invention is accordingly a process for preparing dialkyl 1,4-cyclohexanedicarboxylates in which the two alkyl groups both have at least 2 carbon atoms, preferably at least 4 carbon atoms, the process comprising at least the ring hydrogenation of a dialkyl terephthalate in which the two alkyl groups both have at least 2 carbon atoms, preferably at least 4 carbon atoms, with a hydrogen-containing gas to form the corresponding dialkyl 1,4-cyclohexanedicarboxylate, wherein the dialkyl terephthalate used in the ring hydrogenation has a CO value of less than 0.3 mg KOH/g, preferably less than 0.2 mg KOH/g, more preferably less than 0.1 mg KOH/g.

The invention also includes the following embodiments:
1. Process for preparing dialkyl 1,4-cyclohexanedicarboxylates in which the two alkyl groups both have at least 2 carbon atoms, preferably at least 4 carbon atoms, the process comprising at least the ring hydrogenation of a dialkyl terephthalate in which the two alkyl groups both have at least 2 carbon atoms, in the presence of a heterogeneous hydrogenation catalyst, with a hydrogen-containing gas to form the corresponding dialkyl 1,4-cyclohexanedicarboxylate, characterized in that the dialkyl terephthalate used in the ring hydrogenation has a CO value of less than 0.3 mg KOH/g, preferably less than 0.2 mg KOH/g, more preferably less than 0.1 mg KOH/g.
2. Process according to Embodiment 1, wherein the two alkyl groups of the dialkyl 1,4-cyclohexanedicarboxylate have 3 to 10 carbon atoms, preferably 4 to 10 carbon atoms, more preferably 5 to 9 carbon atoms, particularly preferably 8 or 9 carbon atoms and most preferably 9 carbon atoms.
3. Process according to Embodiment 1 or 2, wherein the dialkyl terephthalate used in the ring hydrogenation is prepared by transesterification of dimethyl terephthalate with an alcohol having at least 2 carbon atoms or by esterification of terephthalic acid with an alcohol having at least 2 carbon atoms.
4. Process according to Embodiment 3, wherein the alcohol used in the transesterification or in the esterification is an alcohol having 3 to 10 carbon atoms, preferably 4 to 10 carbon atoms, more preferably having 5 to 9 carbon atoms, particularly preferably having 8 or 9 carbon atoms and most preferably having 9 carbon atoms.
5. Process according to Embodiment 2 or 4, wherein the dialkyl 1,4-cyclohexanedicarboxylate is diisononyl 1,4-cyclohexanedicarboxylate or di-2-ethylhexyl 1,4-cyclohexanedicarboxylate.
6. Process according to any of Embodiments 1 to 5, wherein the heterogeneous hydrogenation catalyst used in the ring hydrogenation comprises a transition metal on a support material.
7. Process according to Embodiment 6, wherein the transition metal is a metal of group 8 of the periodic table of the elements (iron group), preferably ruthenium.
8. Process according to Embodiment 6, wherein the support material is selected from the group consisting of activated carbon, silicon carbide, aluminium oxide, silicon dioxide, aluminosilicate, titanium dioxide, zirconium dioxide, magnesium oxide, zinc oxide or mixtures thereof.
9. Process according to Embodiment 8, wherein the support material is titanium dioxide or aluminium oxide.
10. Process according to any of Embodiments 6 to 9, wherein the transition metal content in the heterogeneous hydrogenation catalyst is within a range from 0.1% to 10% by weight, preferably in particular within a range from 0.5% to 5% by weight, particularly within a range from 1% to 3% by weight.

11. Process according to any of Embodiments 1 to 10, wherein the ring hydrogenation is carried out in at least one hydrogenation unit, preferably in at least two hydrogenation units connected in series, wherein at least one of the at least two hydrogenation units is operated in loop mode.
12. Process according to any of Embodiments 1 to 11, wherein the hydrogenation temperature in the ring hydrogenation is within a range from 50 to 250° C.
13. Process according to any of Embodiments 1 to 12, wherein the ring hydrogenation is carried out within a pressure range from 3 to 300 bar.
14. Use of the dialkyl 1,4-cyclohexanedicarboxylates prepared according to any of Embodiments 1 to 13 as plasticizers or as a component of a plasticizer composition in plastics or plastic compositions.
15. Use of the dialkyl 1,4-cyclohexanedicarboxylates prepared according to any of Embodiments 1 to 13 as an additive in paints or varnishes, in adhesives or adhesive components, in sealants or as solvents.

DETAILED DESCRIPTION OF THE INVENTION

The CO value is defined as the amount of KOH in milligrams equivalent to the amount of hydroxylamine necessary for the oximation of 1 g of substance. The CO value is determined by reacting the substance dissolved in carbonyl-free alcohol with an excess of hydroxylamine to form the corresponding oxime and back-titrating the unused hydroxylamine with hydrochloric acid.

In order to determine the CO value, the equivalence point must first be determined using a calibration solution. For this, calibration solutions containing varying amounts of cyclohexanone in a suitable solvent, e.g. carbonyl-free methanol, are prepared. The theoretical CO value is given by the following formula:

$$\text{CO value (theoretical)} = \frac{\text{Molar mass of KOH} \cdot \text{Purity of cyclohexanone}}{\text{Molar mass of cyclohexanone}}$$

The calibration solutions prepared are each titrated with 0.1 mol/l hydrochloric acid. The measured pH is then plotted as function of the volume of hydrochloric acid consumed in each case and the equivalence point is determined. This results in calibration of the system.

The CO value of an unknown sample can then be determined as follows. A reaction vessel is first charged with an appropriate amount of sample and this is dissolved in 50 ml of a suitable solvent, e.g. carbonyl-free methanol. The solvent used, e.g. methanol, must first undergo a blank determination without sample as described below. Bromophenol blue is added to the solution of the sample in the solvent, e.g. methanol, and the pH is if necessary adjusted by adding hydrochloric acid or sodium hydroxide solution such that the solution has a green-yellow colour (corresponding to a pH of about 3). 20 ml of hydroxylamine solution (c=0.24 mol/l) is then metered in and the resulting solution in the reaction vessel is boiled under reflux for 1 h.

After cooling to room temperature, the reflux condenser is rinsed with 10 ml of solvent, e.g. carbonyl-free methanol, and the reaction solution then titrated to the equivalence point with 0.1 mol/l hydrochloric acid.

The CO value can then be determined according to the following formula:

$$\text{CO value (mg KOH/g)} = \frac{(V_B - V_H) \cdot F_{HCl} \cdot c_{HCl} \cdot M_{KOH}}{W_S}$$

where $V_B$ is the volume of hydrochloric acid consumed in the blank determination in ml, $V_H$ is the volume of hydrochloric acid consumed in the analysed sample in ml, $F_{HCl}$ is the titre of the hydrochloric acid, $c_{HCl}$ is the concentration of the hydrochloric acid in mol/l, $M_{KOH}$ is the molar mass of KOH=56.11 g/mol and $W_S$ is the sample weight in g.

Provided it is ensured that the dialkyl terephthalate used in the ring hydrogenation has a CO value of less than 0.3, the ring hydrogenation can be carried out with greater rapidity. Of the dialkyl 1,4-cyclohexanedicarboxylates thereby produced, in which the alkyl groups both have at least 2 carbon atoms, preferably at least 4 carbon atoms, preference is given to dialkyl 1,4-cyclohexanedicarboxylates in which the alkyl groups both have 3 to 10 carbon atoms, more preferably 4 to 10 carbon atoms, more preferably 5 to 9 carbon atoms, particularly preferably 8 or 9 carbon atoms and most preferably 9 carbon atoms.

The ring hydrogenation of dialkyl terephthalates is known in principle to those skilled in the art. The ring hydrogenation is carried out with a hydrogen-containing gas. The hydrogen-containing gas used may in principle be any hydrogen-containing gas mixtures that do not contain harmful amounts of catalyst poisons such as carbon monoxide or hydrogen sulfide. It is also possible to use gas mixtures with inert gases. The hydrogen-containing gas used is preferably hydrogen having a purity of ≥95%, in particular ≥98%. Inert gas fractions may be, for example, nitrogen or methane. The hydrogen-containing gas is preferably used such that the hydrogen is in excess, in particular in an excess of up to 200%, preferably in an excess of 5 to 100% and more preferably in an excess of 10 to 50%, based on the stoichiometric amount needed to achieve the desired conversion.

The ring hydrogenation of the invention additionally employs heterogeneous hydrogenation catalysts preferably containing at least one transition metal, more preferably a metal of group 8 of the periodic table of the elements. Preference as the transition metal used is given to platinum, rhodium, palladium, cobalt, nickel or ruthenium or a mixture of two or more thereof, ruthenium being particularly preferred as the active metal. In addition to the metals already mentioned, at least one metal of group 7 and 11 of the periodic table of the elements may additionally be present in the catalysts. Preference is given to using rhenium and/or copper.

The transition metal content in the hydrogenation catalyst of the invention is preferably within a range from 0.1% to 10% by weight, in particular within a range from 0.5% to 5% by weight, most preferably within a range from 0.5% to 2% by weight.

The heterogeneous hydrogenation catalysts used are preferably supported catalysts, i.e. they comprise a support material. Support materials used may be activated carbon, silicon carbide, aluminium oxide, silicon dioxide, aluminosilicate, titanium dioxide, zirconium dioxide, magnesium oxide, zinc oxide or mixtures thereof. Particular preference is given to using titanium dioxide or aluminium oxide as the support material. In addition, these support materials may comprise alkali metals, alkaline earth metals and/or sulfur.

The ring hydrogenation of dialkyl terephthalates according to the invention is preferably carried out in at least one hydrogenation unit. A hydrogenation unit is in the present invention understood as meaning a unit comprising one or more reactors that may be connected in parallel and/or in series, in other words a reactor or a reactor assembly in which the ring hydrogenation takes place. In a particularly preferred embodiment, the ring hydrogenation is carried out in at least two hydrogenation units connected in series, wherein at least one of the two hydrogenation units is operated in loop mode, i.e. with part of the output from the respective hydrogenation being recycled. It can be advantageous when all of the at least two hydrogenation units in the ring hydrogenation are operated in loop mode. It can likewise be advantageous when the final hydrogenation unit is operated in straight pass.

In a particularly preferred embodiment, the ring hydrogenation is carried out in at least three hydrogenation units connected in series with at least the first two hydrogenation units operated in loop mode. The final hydrogenation unit may be operated in loop mode too, which thus corresponds to an embodiment in which all of the at least three hydrogenation units are operated in loop mode. The final hydrogenation unit may likewise be operated in straight pass.

A further particularly preferred embodiment is the parallel arrangement of the reactors, for example in a tube bundle reactor.

The individual reactors may in this case be operated adiabatically, polytropically or practically isothermally, i.e. with a temperature increase (difference of the temperature at the inlet and temperature at the outlet of the reactor) of typically less than 15 K. The reactors operated in loop mode in particular are operated preferably quasi-isothermally, that is to say preferably operated with a temperature increase of less than 15 K. In reactors not operated in loop mode, the temperature increase in the reactor is preferably under 35 K, more preferably under 25 K. Between individual hydrogenation elements may be fitted a cooling apparatus to lower the temperature prior to entry into the following hydrogenation unit.

The ring hydrogenation of dialkyl terephthalates according to the invention is preferably carried out in cocurrent in the liquid/gas mixed phase or liquid phase in three-phase reactors, the hydrogen-containing gas being distributed in the liquid reactant/product stream in a manner known per se. In the interests of a uniform liquid distribution, of improved dissipation of the heat of reaction and/or of a high space-time yield, the reactors operated in loop mode are preferably operated with high liquid loads of from 10 to 400, preferably from 20 to 200 and particularly preferably from 40 to 150, $m^3$ per $m^2$ cross section of the empty reactor per hour. The liquid loads may in the reactors operated in loop mode be the same or different. The liquid load is preferably greatest in the first reactor and decreases in the subsequent reactors operated in loop mode. One or more reactors may here be partially flooded with liquid or may function wholly as trickle-bed reactors.

The ring hydrogenation of dialkyl terephthalates may be carried out in the absence of a solvent or in the presence thereof. The solvent used may be all liquids that form a homogeneous solution with the reactant and product, are inert under hydrogenation conditions and can be easily removed from the product. The solvent may also be a mixture of two or more substances and may optionally comprise water. The following substances may be used as solvent in the ring hydrogenation: straight-chain or cyclic ethers such as tetrahydrofuran or dioxane and also aliphatic alcohols in which the alkyl radical has 1 to 13 carbon atoms. Alcohols that may be used with preference as solvent are isopropanol, n-butanol, isobutanol, n-pentanol, 2-ethylhexanol, nonanols, technical nonanol mixtures, decanol, technical decanol mixtures, tridecanols. When using alcohols as solvent, it can be expedient to use the alcohol or alcohol mixture that would be formed in the hydrolysis of the product. This would rule out by-product formation through transesterification. A further preferred solvent is the hydrogenation product itself.

The use of a solvent allows the reactant concentration in the reactor feed to be limited, as a result of which better temperature control in the reactor can be achieved. This can minimize side reactions and accordingly bring about an increase in product yield. The reactant content in the reactor feed is preferably between 1 and 70%. The desired concentration range in the reactors operated in loop mode can be adjusted through the circulation ratio (molar ratio of recycled hydrogenation output to reactant). The reactant concentration in the reactor feed preferably decreases from the first to the last reactor.

The ring hydrogenation of dialkyl terephthalates is according to the invention preferably carried out within a pressure range from 3 to 300 bar, in particular from 15 to 200 bar, most preferably from 50 to 200 bar. The pressure in the individual reactors may be the same or different. The pressures are preferably the same or approximately the same, i.e. differing from one another by a maximum of 10%.

The hydrogenation temperatures in the ring hydrogenation are preferably within a range from 50 to 250° C., preferably within a range from 80 to 200° C. The hydrogenation temperatures in individual reactors may be the same or different.

The products obtained in the process of the invention are corresponding compositions that are dependent on the feedstocks and on the conversion in the hydrogenation. The composition formed in the ring hydrogenation of the invention preferably has a content of dialkyl 1,4-cyclohexanedicarboxylates of over 96% by weight, in particular of over 98% by weight, particularly preferably of over 99% by weight. This mixture may be used directly or after purification. By-products may be removed for example by distillation or by stripping with steam or with an inert gas such as nitrogen. Small amounts of low boilers are preferably removed by stripping with steam within a temperature range from 120° C. to 240° C., in particular within a range from 150 to 200° C., and preferably at a pressure of 0.05 to 0.1 bar.

The dialkyl terephthalates used in the ring hydrogenation, in which the two alkyl groups have at least 2 carbon atoms, preferably at least 4 carbon atoms, may be prepared by transesterification of dimethyl terephthalate with an alcohol or alcohol mixtures having more than 2 carbon atoms, preferably having 3 to 10 carbon atoms, more preferably having 4 to 10 carbon atoms, more preferably having 5 to 9 carbon atoms, particularly preferably having 8 or 9 carbon atoms and most preferably having 9 carbon atoms. A further option for preparing the dialkyl terephthalates used in the ring hydrogenation is esterification of terephthalic acid with an alcohol or an alcohol mixture having more than 2 carbon atoms, preferably having 3 to 10 carbon atoms, more preferably having 4 to 10 carbon atoms, more preferably having 5 to 9 carbon atoms, particularly preferably having 8 or 9 carbon atoms and most preferably having 9 carbon atoms. Both processes are known in principle to those skilled in the art.

The transesterification of dimethyl terephthalate is carried out catalytically, preferably using acids or bases (Brønsted or Lewis) as catalyst. Irrespective of which catalyst is used, a temperature-dependent equilibrium is always reached between the feedstocks (dimethyl terephthalate and alcohol) and the products (dialkyl terephthalate and methanol liberated from the dimethyl terephthalate used). In order to shift the equilibrium in favour of the dialkyl terephthalate, it may be advantageous to distil out of the reaction mixture the methanol formed from the dimethyl terephthalate reactant.

In the transesterification it may be additionally advantageous to use the alcohol in an excess overall. The employed alcohol having more than 2 carbon atoms is preferably used in an excess of 5 to 50%, preferably 10 to 30%, of the molar amount necessary for formation of the dialkyl terephthalate of the invention.

The transesterification catalysts used may be acids, such as sulfuric acid, methanesulfonic acid or p-toluenesulfonic acid, or metals or compounds thereof. Examples of suitable metals or compounds thereof are tin, titanium, zirconium, which are used as the finely divided metal or expediently in the form of salts thereof, as oxides, or in the form of soluble organic compounds. The metal catalysts are, by comparison with catalysts based on protic acids, high-temperature catalysts that often attain their full activity only at temperatures above 180° C. To minimize or avoid the formation of by-products, it may however be advantageous to use metal catalysts based on metals or compounds thereof. Examples of particularly preferably employed metal catalysts are tin powder, tin(II) oxide, tin(II) oxalate, titanic esters such as tetraisopropyl orthotitanate or tetrabutyl orthotitanate, and also zirconium esters such as tetrabutyl zirconate. It is additionally possible to use basic catalysts such as oxides, hydroxides, hydrogen carbonates, carbonates or alkoxides of alkali metals or alkaline earth metals. From this group, preference is given to using alkoxides such as sodium methoxide. Alkoxides may also be produced in situ from an alkali metal and an alcohol such as nonanol or an isononanol mixture. Particular preference is given to using alkoxides in which the alcohol residue corresponds to one of the alcohols taking part in the reaction.

The catalyst concentration may be varied within wide ranges and particularly in accordance with the nature of the catalyst. The catalyst concentration is preferably from 0.005% to 2.0% by weight based on the reaction mixture. The optimal concentrations for each catalyst can be easily determined through preliminary experiments and arise from a trade-off between minimizing catalyst consumption (cost factor) and maximizing the rate of reaction. In the case of the tetrabutyl orthotitanate catalyst employed with particular preference according to the invention, the preferred concentration is for example within a range from 0.005% to 1% by weight based on the dimethyl terephthalate used.

The transesterification is preferably carried out at a temperature of 100 to 240° C. The pressure during the transesterification may be between 0.1 and 10 bar. The chosen temperature is particularly preferably sufficiently high that the alcohol formed from the ester reactant can be distilled out of the reaction mixture at the specified pressure.

The crude ester mixtures produced can be processed in the same way as those produced by the esterification of terephthalic acid described hereinbelow.

The preparation of the dialkyl terephthalates of the invention by esterification of terephthalic acid with an alcohol or alcohol mixture having at least 2 carbon atoms, preferably having at least 4 carbon atoms, can be carried out according to all known methods. The esterification is however preferably carried out according to a process in which the water of reaction is removed by azeotropic distillation with the alcohol and the amount of liquid removed from the reaction by the azeotropic distillation is replenished in full or in part by the alcohol used. The amount of liquid is described hereinbelow as the volume of liquid, mainly consisting of water of reaction and alcohol, that is removed from the reaction by azeotropic distillation. Full replacement of the amount of liquid removed is preferable.

The esterification of terephthalic acid to dialkyl terephthalates may according to the invention be carried out with autocatalysis or with acid or base catalysis. Esterification catalysts used may be Lewis or Brønsted acids or metalorganic substances. Preferred esterification catalysts are alkoxides, sulfonic acids, carboxylate salts or chelate compounds of titanium or zirconium, wherein the catalyst molecule may contain one or more metal atoms. Tetraisopropyl orthotitanate and tetrabutyl orthotitanate are in particular used. The catalyst concentration depends on the nature of the catalyst. In the case of the titanium compounds used with preference, this is 0.005% to 1.0% by weight based on the reaction mixture, in particular 0.01% to 0.3% by weight.

The esterification of the invention is preferably carried out in a reaction vessel in which the reaction mixture can be intensively mixed with the aid of a stirrer or a circulation pump. The reactants and the catalyst may be fed into the reactor at the same time or one after the other. The catalyst may be introduced in pure form or as a solution, preferably dissolved in one of the feedstocks, either at the start or only once the reaction temperature has been reached. The alcohol to be used, which acts as the azeotroping agent, may be used in a stoichiometric excess. It is preferable to use an excess of 5 to 50%, more preferably 10 to 30%, based on the terephthalic acid used.

The reaction temperatures when using titanium catalysts are between 120° C. and 270° C., preferably between 130° C. and 270° C. The optimal temperatures depend on the feedstocks, progress of the reaction and the catalyst concentrations. They may be readily determined for each individual case through experiments. Higher temperatures increase the rates of reaction and favour side reactions such as elimination of water from alcohols or formation of coloured by-products.

The amount of liquid to be recycled into the reaction may consist in part or in full of alcohol obtained by processing the azeotropic distillate. It is also possible for processing to be carried out at a later time and for the amount of liquid removed to be replaced in full or in part with fresh alcohol, i.e. alcohol available from a reservoir vessel. In other embodiments of the esterification, the removed liquid is processed into the alcohol, preferably into the pure alcohol.

At the end of the reaction, the reaction mixture, which consists largely of the target product dialkyl terephthalate and excess alcohol, also additionally contains catalyst and/or conversion products thereof and/or small amounts of carboxylic acid. For processing of these crude mixtures, the excess alcohol is removed, the acidic compounds are neutralized, the catalyst is destroyed and the solid by-products thereby formed are separated off. The main part of the alcohol is here distilled off at standard pressure or under reduced pressure. The last traces of the alcohol may be removed e.g. by steam distillation or sparging with nitrogen, in particular within a temperature range from 120 to 225° C. The removal of the alcohol may for example be carried out as the first or as the last step in processing.

Acidic substances such as carboxylic acids, hemiesters or—where used—acidic catalysts may be neutralized by adding basic compounds of the alkali metals and/or alkaline earth metals. These may be used in the form of the carbonates, hydrogen carbonates or hydroxides thereof. The neutralizing agent may be used in solid form or preferably as a solution, in particular as an aqueous solution. The neutralization may be carried out immediately after the end of the esterification reaction or after distilling off the main part of the excess alcohol. Preference is given to neutralizing with sodium hydroxide solution immediately after the end of the esterification reaction at temperatures above 150° C. The water introduced with the alkali may then be distilled off together with the alcohol.

Given that terephthalic acid is only sparingly soluble in the alcohol(s) to be used for the esterification, even at the boiling point, the solubility, and hence the rate of reaction, can be increased further through an overpressure of max. 20 bar, preferably max. 10 bar, as a consequence of the higher boiling point. When using dimethyl terephthalate for the transesterification, these problems are absent. If starting from dimethyl terephthalate, the corresponding terephthalate can generally be obtained after shorter times than when terephthalic acid is used as starting material. The preparation of the dialkyl terephthalates used in the ring hydrogenation by transesterification starting from dimethyl terephthalate is therefore particularly preferable.

The alcohol used for preparing the dialkyl terephthalate in the transesterification or in the esterification is an alcohol or alcohol mixture having at least 2 carbon atoms, preferably at least 4 carbon atoms. Preference is given to alcohols having 3 to 10 carbon atoms, more preferably having 4 to 10 carbon atoms, more preferably having 5 to 9 carbon atoms, particularly preferably having 8 or 9 carbon atoms and most preferably having 9 carbon atoms. The alcohols used are in particular primary alcohols, in particular ethanol, propanol, butanol, pentanol, hexanol, heptanol, octanol, preferably 2-ethylhexanol, nonanol, preferably isononanol/mixtures of isomeric nonanols, 2-propylheptanol or decanol. The alcohol used in the esterification is particularly preferably 2-ethylhexanol or isononanol.

The dialkyl 1,4-cyclohexanedicarboxylates prepared according to the invention, in which the two alkyl groups both have at least 2 carbon atoms, preferably at least 4 carbon atoms, can be advantageously used as plasticizers or as a component of a plasticizer composition in plastics or plastic compositions, as an additive in paints or varnishes, in adhesives or adhesive components, in sealants or as solvents.

The dialkyl 1,4-cyclohexanedicarboxylates produced can also be used as plasticizers in mixtures with other plasticizers, in particular so-called fast fusers. The proportion of dialkyl 1,4-cyclohexanedicarboxylates of the invention in the mixture with other plasticizers is preferably 15% to 95% by weight, more preferably 20% to 90% by weight and most preferably 25% to 85% by weight, the proportions of all the plasticizers present adding up to 100% by weight. The above compositions from dialkyl 1,4-cyclohexanedicarboxylates and other plasticizers can be used as a plasticizer composition in plastics and plastic compositions, adhesives, sealants, varnishes, paints, plastisols or inks.

The plastic compositions that may comprise the dialkyl 1,4-cyclohexanedicarboxylates produced may comprise polymers selected from polyvinyl chloride (PVC), polyvinylidene chloride (PVDC), polyacrylates, in particular polymethyl methacrylate (PMMA), polyalkyl methacrylate (PAMA), fluoropolymers, in particular polyvinylidene fluoride (PVDF), polytetrafluoroethylene (PTFE), polyvinyl acetate (PVAc), polyvinyl alcohol (PVA), polyvinyl acetals, in particular polyvinyl butyral (PVB), polystyrene polymers, in particular polystyrene (PS), expandable polystyrene (EPS), acrylonitrile-styrene acrylate (ASA), styrene-acrylonitrile (SAN), acrylonitrile-butadiene-styrene (ABS), styrene-maleic anhydride copolymer (SMA), styrene-methacrylic acid copolymer, polyolefins, in particular polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulfide (PSu), biopolymers, in particular polylactic acid (PLA), polyhydroxybutyric acid (PHB), polyhydroxyvaleric acid (PHV), polyesters, starch, cellulose and cellulose derivatives, in particular nitrocellulose (NC), ethylcellulose (EC), cellulose acetate (CA), cellulose acetate/butyrate (CAB), rubber or silicones and also mixtures or copolymers of the above polymers or of the monomeric units thereof. The compositions of the invention preferably include PVC or homo- or copolymers based on ethylene, propylene, butadiene, vinyl acetate, glycidyl acrylate, glycidyl methacrylate, methacrylates, acrylates, acrylates or methacrylates in which are attached at the oxygen atom of the ester group alkyl residues from branched or unbranched alcohols having one to ten carbon atom(s), styrene, acrylonitrile or cyclic olefins.

Particular preference is given to the use of PVC.

As the PVC type, the plastic composition of the invention preferably comprises suspension PVC, bulk PVC, microsuspension PVC or emulsion PVC. Based on 100 parts by weight of polymer, the compositions of the invention contain preferably from 5 to 200, more preferably from 10 to 150, parts by weight of plasticizer of the invention.

In addition to the constituents mentioned, the plastic compositions may comprise other constituents, in particular e.g. further plasticizers, fillers, pigments, stabilizers, co-stabilizers, such as epoxidized soybean oil, lubricants, blowing agents, kickers, antioxidants, rheology additives or biocides.

The plastic compositions of the invention obtained from dialkyl 1,4-cyclohexanedicarboxylates and the abovementioned polymer materials may be used as plastic compositions, adhesives, sealants, varnishes, paints, plastisols, imitation leather, floor coverings, underbody protection, fabric coatings, roof membranes, wallpapers or inks or in the production thereof.

The plastic products produced with the plasticizer compositions can for example be profiles, gaskets, food packaging, films, toys, medical devices, roof sheeting, imitation leather, floor coverings, underbody protection, coated fabrics, roof membranes, wallpapers, cabling and wire sheathings. Preferred fields of use from this group are food packaging, toys, medical devices, wallpapers, roof membranes, fabric coatings and floor coverings.

The invention is illustrated hereinbelow by examples. The examples are selected embodiments and do not constitute any restriction.

Example 1: Ring Hydrogenation of Diisononyl Terephthalate

To examine the dependence of the duration of the ring hydrogenation of diisononyl terephthalate, various DINT samples were tested in a ring hydrogenation. The following samples were used:

Origin of the various DINT samples:

DINT-1

2.318 g (16.1 mol) of isonyl alcohol (INA, Evonik, purity >99%), 1.358 g (7 mol) of dimethyl terephthalate (Oxxynova, purity >99.9%) and 2.4 g of tetra-n-butyl titanate catalyst were heated to 240° C. under a nitrogen atmosphere (nitrogen flow: 6 L/h) in a 6 L glass flask with stirrer, dip tube and Raschig ring column with attached condenser, during which distillate was taken off while ensuring the column overhead temperature did not rise above 65° C. The course of the reaction was monitored by gas chromatography and the reaction terminated once the residual concentration of methyl esters was <0.5%. After a reaction time of 3 h, the bottoms temperature was lowered to 220° C. and the pressure progressively reduced in order to distil off the excess alcohol.

The column was then replaced by a distillation bridge, 4 g of 10% NaOH solution and 20 ml of demineralized water were added at 80° C. and the mixture was stirred for 15 min to destroy the catalyst. The reaction mixture was then heated to 180° C. and dried under full vacuum for 40 min, followed by stripping with nitrogen at 20 mbar for 2 h. After checking the residual alcohol content by GC, the mixture was cooled to 80° C. and filtered.

The reaction product diisononyl terephthalate (DINT) was obtained in a purity of 99.96%. The CO value was determined according to the method given in the description and was 0.03 mg KOH/g.

DINT-2

2.318 g (16.1 mol) of isononyl alcohol (INA, Evonik, purity >99%), 1.163 g (7 mol) of terephthalic acid (Acros Organics, purity >99%) and 2.4 g of tetra-n-butyl titanate catalyst were heated to 240° C. under a nitrogen atmosphere (nitrogen flow: 6 L/h) in a 6 L glass flask with stirrer, dip tube, condenser and water separator. To speed up the removal of water from the reaction system, 140 ml of cyclohexane was added as an azeotroping agent. The esterification was terminated after 11.5 h.

At the end of the reaction and after cooling to room temperature, the water separator was replaced by a distillation bridge and the residual alcohol distilled off at 180° C. under full vacuum (approx. 1-3 mbar). 1.9 g of 10% NaOH solution and 20 ml of demineralized water were then added at 80° C. and the mixture was stirred for 15 min to destroy the catalyst. The reaction mixture was then heated to 180° C. and dried under full vacuum for 40 min, followed by stripping with nitrogen at 20 mbar for 2 h. After checking the residual alcohol content by GC, the mixture was cooled to 80° C. and filtered.

The reaction product diisononyl terephthalate (DINT) was obtained in a purity of 99.75%. The CO value was determined according to the method given in the description and was 0.06 mg KOH/g.

DINT-3

In a nitrogen-filled industrial-scale reactor having a capacity of approx. 50 m$^3$, 27 t of isononanol (INA, Evonik, purity >99%) was preheated to approx. 145° C. and then 5 kg of tetra-n-butyl titanate catalyst and 18 t of dimethyl terephthalate (Oxxynova, purity >99.9%) were added. The reaction mixture was heated further up to max. 220° C., during which methanol was taken off via a distillation column. The course of the reaction was monitored by gas chromatography and the reaction terminated once the residual concentration of methyl esters was <0.5%.

As soon as the reaction was complete, the return flow at the column head was stopped and a vacuum (approx. 50-100 mbar) applied to the reactor. In the next steps proceeding in parallel, the catalyst was destroyed with 25% NaOH solution and free acid neutralized.

The DINT produced was dried at approx. 130° C. under full vacuum (approx. 50 mbar) and then filtered. The reaction product diisononyl terephthalate (DINT) was obtained in a purity of 99.7%. The CO value was determined according to the method given in the description and was 0.07 mg KOH/g.

DINT-4 is the product UN499 from UPC, Taiwan. The CO value was determined according to the method given in the description and was 0.21 mg KOH/g.

DINT-6 is a mixture of DINT-4 (60% by weight) and DINT-6 (40% by weight). The CO value was determined according to the method given in the description and was 0.43 mg KOH/g.

DINT-6 is the product Kanatol-9090 from KU Group, India. The CO value was determined according to the method given in the description and was 0.57 mg KOH/g.

Ring Hydrogenation of DINT Samples

Batch hydrogenation of various DINT (diisononyl terephthalate) samples was carried out in loop operation in a tubular reactor having an internal diameter of 40 mm and a length of 190 mm. In this process, liquid phase and gas phase flow through the tubular reactor in cocurrent flow in the trickle bed. The catalyst used in the hydrogenation was a shell catalyst consisting of 1% by weight Ru supported on titanium dioxide (Aerolyst 7711). Employed in the tubular reactor were in each case 25 g of hydrogenation catalyst and also 25 g of inert material, consisting of $Al_2O_3$, in the form of 1.5 mm extrudates. The amount of DINT used in the hydrogenation was always 1000 g. The $H_2$ was regulated via a constant offgas operating mode in which the offgas was set at a constant flow of 1 L/h (47.8 m$^3$ m$^{-2}$ h$^{-1}$). All experiments were carried out at a system pressure of 90 bar and a tubular reactor temperature of 110° C. After passing a heat exchanger beneath the reactor, a gas-liquid separation is effected by a separator. The gas phase is continuously released into the offgas. The liquid phase is recycled via a heated prewarmer into the tubular reactor, where renewed hydrogenation with $H_2$ can take place. The DINT concentration over time was recorded by inline Raman analysis.

The results are shown in Table 1 below.

TABLE 1

Concentration of DINT as a function of time during the hydrogenation

| Sample | CO value | c (DINT)* 0 h | c (DINT) 2 h | c (DINT) 4 h | c (DINT) 8 h | c (DINT) 12 h |
|---|---|---|---|---|---|---|
| DINT-1 | 0.03 | 100 | 66.3 | 40.5 | 10.6 | 1.6 |
| DINT-2 | 0.06 | 100 | 71.1 | 47.3 | 16.3 | 3.7 |
| DINT-3 | 0.07 | 100 | 71.9 | 49.1 | 17.0 | 3.5 |
| DINT-4 | 0.21 | 100 | 76.3 | 57.1 | 27.3 | 9.6 |
| DINT-5 | 0.43 | 100 | 80.3 | 64.0 | 36.5 | 17.2 |
| DINT-6 | 0.57 | 100 | 87.9 | 75.9 | 53.7 | 34.9 |

*the concentration c (DINT) is normalized to 100%.

From the table it can be seen that a significantly faster ring hydrogenation takes place when using DINT having a CO value within the recited range.

The invention claimed is:

1. A process for preparing dialkyl 1,4-cyclohexanedicarboxylate in which the two alkyl groups both have at least 2 carbon atoms, the process comprising:
   carrying out a ring hydrogenation of a dialkyl terephthalate in which the two alkyl groups both have at least 2 carbon atoms, in the presence of a heterogeneous hydrogenation catalyst, with a hydrogen-containing gas, to form the dialkyl 1,4-cyclohexanedicarboxylate, wherein the dialkyl terephthalate in the ring hydrogenation has a CO value of less than 0.3 mg KOH/g.

2. The process according to claim 1, wherein each of the two alkyl groups of the dialkyl 1,4-cyclohexanedicarboxylate have 3 to 10 carbon atoms.

3. The process according to claim 1, wherein the dialkyl terephthalate in the ring hydrogenation is prepared by transesterification of dimethyl terephthalate with an alcohol having at least 2 carbon atoms, or by esterification of terephthalic acid with an alcohol having at least 2 carbon atoms.

4. The process according to claim 3, wherein the alcohol in the transesterification or in the esterification is an alcohol having 3 to 10 carbon atoms.

5. The process according to claim 2, wherein the dialkyl 1,4-cyclohexanedicarboxylate is diisononyl 1,4-cyclohexanedicarboxylate or di-2-ethylhexyl 1,4-cyclohexanedicarboxylate.

6. The process according to claim 1, wherein the heterogeneous hydrogenation catalyst in the ring hydrogenation comprises a transition metal on a support material.

7. The process according to claim 6, wherein the transition metal is a metal of group 8 of the periodic table of the elements.

8. The process according to claim 6, wherein the support material is selected from the group consisting of activated carbon, silicon carbide, aluminium oxide, silicon dioxide, aluminosilicate, titanium dioxide, zirconium dioxide, magnesium oxide, zinc oxide, and mixtures thereof.

9. The process according to claim 8, wherein the support material is titanium dioxide or aluminium oxide.

10. The process according to claim 6, wherein a transition metal content in the heterogeneous hydrogenation catalyst is within a range from 0.1% to 10% by weight.

11. The process according to claim 1, wherein the ring hydrogenation is carried out in at least one hydrogenation unit.

12. The process according to claim 1, wherein a hydrogenation temperature in the ring hydrogenation is within a range from 50 to 250° C.

13. The process according to claim 1, wherein the ring hydrogenation is carried out within a pressure range from 3 to 300 bar.

14. The process according to claim 1, wherein each of the two alkyl groups of the dialkyl 1,4-cyclohexanedicarboxylate have at least 4 carbon atoms.

15. The process according to claim 1, wherein the dialkyl terephthalate in the ring hydrogenation has a CO value of less than 0.1 mg KOH/g.

16. The process according to claim 2, wherein each of the two alkyl groups of the dialkyl 1,4-cyclohexanedicarboxylate have 9 carbon atoms.

17. The process according to claim 7, wherein the transition metal is ruthenium.

18. The process according to claim 11, wherein the ring hydrogenation is carried out in at least two hydrogenation units connected in series, wherein at least one of the at least two hydrogenation units is operated in loop mode.

19. The process according to claim 1, wherein a hydrogenation temperature in the ring hydrogenation is within a range from 80 to 200° C. and ring hydrogenation is carried out within a pressure range from 50 to 200 bar.

* * * * *